(12) United States Patent
Gerbec et al.

(10) Patent No.: US 11,622,864 B2
(45) Date of Patent: Apr. 11, 2023

(54) EXPANDABLE INTERVERTEBRAL IMPLANT

(71) Applicant: Innovasis, Inc., Salt Lake City, UT (US)

(72) Inventors: Daniel E. Gerbec, Logan, UT (US); James Robbins, Logan, UT (US); Eric Wieser, Salt Lake City, UT (US); Ronald K. Groberg, Clearfield, UT (US); Brent A. Felix, Sandy, UT (US)

(73) Assignee: Innovasis, Inc., Salt Lake City, UT (US)

( * ) Notice: Subject to any disclaimer, the term of this patent is extended or adjusted under 35 U.S.C. 154(b) by 0 days.

(21) Appl. No.: 16/912,463

(22) Filed: Jun. 25, 2020

(65) Prior Publication Data
US 2020/0405499 A1 Dec. 31, 2020

Related U.S. Application Data

(60) Provisional application No. 62/868,618, filed on Jun. 28, 2019.

(51) Int. Cl.
*A61F 2/44* (2006.01)
*A61F 2/30* (2006.01)

(52) U.S. Cl.
CPC .. *A61F 2/4425* (2013.01); *A61F 2002/30421* (2013.01); *A61F 2002/30525* (2013.01); *A61F 2002/443* (2013.01)

(58) Field of Classification Search
CPC .. A61F 2/4425; A61F 2/442; A61F 2002/443; A61F 2/4455
See application file for complete search history.

(56) References Cited

U.S. PATENT DOCUMENTS

| 4,309,777 | A |  | 1/1982 | Patil |
| 4,759,769 | A | * | 7/1988 | Hedman ............... A61F 2/4425 |
|  |  |  |  | 623/17.13 |
| 5,458,642 | A |  | 10/1995 | Beer et al. |
| 6,190,414 | B1 | * | 2/2001 | Young .................. A61F 2/4611 |
|  |  |  |  | 623/17.15 |
| 6,193,756 | B1 |  | 2/2001 | Studer et al. |
| 6,200,348 | B1 |  | 3/2001 | Biedermann et al. |
| 6,730,088 | B2 |  | 5/2004 | Yeh |
| 7,094,257 | B2 |  | 8/2006 | Mujwid et al. |
| 7,204,853 | B2 |  | 4/2007 | Gordon et al. |
| 7,217,291 | B2 |  | 5/2007 | Zucherman et al. |

(Continued)

*Primary Examiner* — Matthew J Lawson
(74) *Attorney, Agent, or Firm* — Workman Nydegger (57) ABSTRACT

An expandable intervertebral implant includes a superior plate having a proximal end, an opposing distal end, and a threaded first hole. An inferior plate has a proximal end, an opposing distal end, and a first bore, the inferior plate at least partially bounding an elongated channel that communicates with the first bore. A first lift screw includes a gear wheel rotatably received within the first bore of the inferior plate and a threaded stem projecting from the gear wheel and being threaded into the first hole of the superior plate. A drive screw is rotatably disposed within the channel of the inferior plate, the drive screw having a worm that engages with the gear wheel such that rotation of the drive screw facilitates rotation of the first lift screw which in turn facilitates movement of the superior plate relative to the inferior plate.

20 Claims, 8 Drawing Sheets

(56) References Cited

U.S. PATENT DOCUMENTS

| | | |
|---|---|---|
| 7,569,074 B2 | 8/2009 | Eisermann et al. |
| 7,641,693 B2 | 1/2010 | Gutlin et al. |
| 7,674,296 B2 | 3/2010 | Rhoda et al. |
| 7,708,779 B2 | 5/2010 | Edie et al. |
| 7,749,270 B2 | 7/2010 | Peterman |
| 7,753,958 B2 | 7/2010 | Gordon et al. |
| D626,233 S | 10/2010 | Cipoletti et al. |
| D643,115 S | 8/2011 | Gonzales et al. |
| 8,303,663 B2 | 11/2012 | Jimenez et al. |
| 8,323,345 B2 | 12/2012 | Sledge |
| 9,044,218 B2 * | 6/2015 | Young .................. A61B 17/025 |
| 9,827,107 B1 * | 11/2017 | Amin .................... A61F 2/4425 |
| 9,839,527 B2 * | 12/2017 | Robinson ................ A61F 2/447 |
| 2001/0012966 A1 | 8/2001 | Studer et al. |
| 2002/0082695 A1 | 6/2002 | Neumann |
| 2002/0161441 A1 | 10/2002 | Lang et al. |
| 2003/0074063 A1 | 4/2003 | Gerbec et al. |
| 2004/0254644 A1 | 12/2004 | Taylor |
| 2005/0010295 A1 | 1/2005 | Michelson |
| 2005/0015149 A1 | 1/2005 | Michelson |
| 2005/0021144 A1 | 1/2005 | Malberg et al. |
| 2005/0261769 A1 | 11/2005 | Moskowitz et al. |
| 2005/0273167 A1 | 12/2005 | Triplett et al. |
| 2006/0122703 A1 | 6/2006 | Aebi et al. |
| 2006/0149383 A1 | 7/2006 | Arnin et al. |
| 2006/0167547 A1 | 7/2006 | Suddaby |
| 2006/0195191 A1 | 8/2006 | Sweeney, II et al. |
| 2006/0265068 A1 | 11/2006 | Schwab |
| 2007/0028710 A1 | 2/2007 | Kraus et al. |
| 2007/0239279 A1 | 10/2007 | Francis |
| 2007/0255415 A1 | 11/2007 | Edit et al. |
| 2007/0288092 A1 | 12/2007 | Bambakidis |
| 2008/0027468 A1 | 1/2008 | Fenton, Jr. et al. |
| 2008/0103601 A1 * | 5/2008 | Biro ...................... A61F 2/4425 623/17.16 |
| 2008/0140207 A1 | 6/2008 | Olmos et al. |
| 2008/0147193 A1 | 6/2008 | Matthis et al. |
| 2009/0210061 A1 * | 8/2009 | Sledge .................. A61F 2/4465 623/17.15 |
| 2009/0222100 A1 | 9/2009 | Cipoletti et al. |
| 2009/0281625 A1 | 11/2009 | Enayati |
| 2010/0082109 A1 | 4/2010 | Greenhalgh et al. |
| 2011/0035011 A1 | 2/2011 | Cain |
| 2011/0160861 A1 * | 6/2011 | Jimenez ................. F16H 25/20 623/17.16 |
| 2011/0172716 A1 * | 7/2011 | Glerum ................ A61F 2/4455 606/279 |
| 2011/0172774 A1 | 7/2011 | Varela |
| 2011/0301714 A1 | 12/2011 | Theofilos |
| 2012/0265303 A1 * | 10/2012 | Refai ...................... A61F 2/44 623/17.11 |
| 2012/0310350 A1 * | 12/2012 | Farris .................... A61F 2/447 623/17.16 |
| 2013/0158668 A1 * | 6/2013 | Nichols ................. A61B 17/56 623/17.16 |
| 2015/0094814 A1 * | 4/2015 | Emerick ............... A61F 2/4611 623/17.16 |
| 2015/0351925 A1 * | 12/2015 | Emerick ................ A61F 2/447 623/17.16 |
| 2016/0089247 A1 * | 3/2016 | Nichols ................ A61F 2/4455 623/17.16 |
| 2018/0133024 A1 * | 5/2018 | Wolters .................... A61F 2/44 |

* cited by examiner

EXPANDABLE INTERVERTEBRAL IMPLANT

CROSS-REFERENCE TO RELATED APPLICATIONS

This application claims the benefit of U.S. Provisional Application No. 62/868,618, filed Jun. 28, 2019, which is incorporated herein by specific reference.

BACKGROUND OF THE DISCLOSURE

1. The Field of the Disclosure

The present disclosure relates to expandable intervertebral implants and, more specifically, to expandable intervertebral implants that incorporate a worm drive and related method of use and assembly.

2. The Relevant Technology

The spinal column is made up of thirty-three vertebra each separated by a cushioning disc. Disease and trauma can damage these discs, creating instability that leads to loss of function and excruciating pain. Spinal fusion implants provide a successful surgical outcome by replacing the damaged disc and restoring the spacing between the vertebrae. The implant also eliminates spinal instability and removes pressure on neurological elements that cause pain. The fusion is accomplished by providing an implant that recreates the natural intervertebral spacing and which has an internal cavity with outwardly extending openings. The internal cavity is commonly filled with an osteogenic material, such as autogenous bone graft or bone allograft, to cause the rapid growth of a bony column through the openings of the implant.

There are a number of different fixed shaped implants that can be placed between adjacent vertebra for fusing the vertebra together. Fixed shaped implants, however, have the disadvantage that a hospital must store and track multiple different sizes of implants since the size of the implant needed can vary based on patient and intended use. Fixed shaped implants can also be difficult to select and position since little tolerance is available.

In an attempt to address some of the shortcoming of fixed shaped implants, adjustable fusion implants have been developed that allow the surgeon to adjust the height of the implant after the implant has been inserted. This provides the ability to intra-operatively tailor the implant height to match the natural spacing between the vertebrae. The ability to adjust the implant reduces the number and sizes of implants that the hospital must keep on hand to match the variable anatomy of the patients. However, adjustable fusion implants have an active mechanism in the form of a mechanical structure for expanding the implant to change its height. The presence of the active mechanism can significantly decrease the amount of internal space available for placement of bone graft and other osteogenic material to encourage the bony fusion between the adjacent vertebrae. Furthermore, the active mechanism can often be complicated and difficult to use. Likewise, an insertion tool used to operate the active mechanism can often be bulky and thereby obscure the insertion, placement, and adjusting of the implant.

Accordingly, what is needed in the art are spinal fusion implants that solve all or some of the above shortcomings and/or other shortcoming that are known in the art.

BRIEF DESCRIPTION OF THE DRAWINGS

Various embodiments of the present disclosure will now be discussed with reference to the appended drawings. It is appreciated that these drawings depict only typical embodiments of the disclosure and are therefore not to be considered limiting of its scope.

DETAILED DESCRIPTION OF THE PREFERRED EMBODIMENTS

Before describing the present disclosure in detail, it is to be understood that this disclosure is not limited to parameters of the particularly exemplified systems, methods, apparatus, products, processes, compositions, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "panel" includes one, two, or more panels. As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to all instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present disclosure may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

Figure 1:
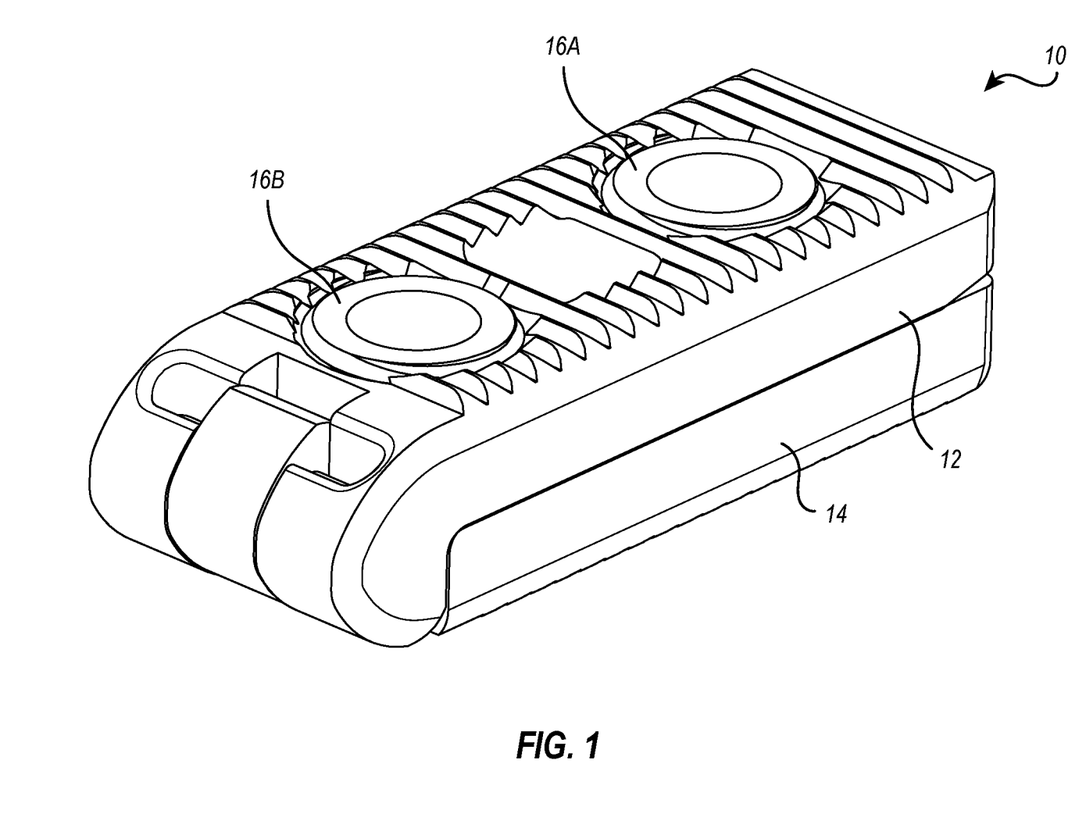
FIG. 1 is a top perspective view of an expandable intervertebral implant in a collapsed state.
Figure 2:
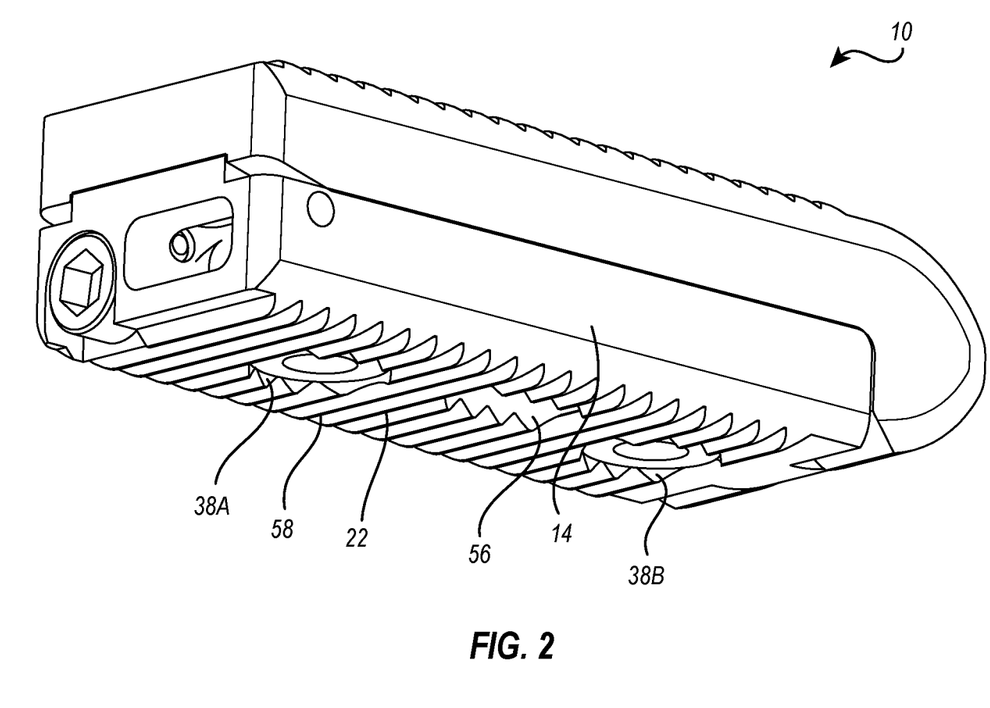
FIG. 2 is a bottom perspective view of the implant shown in FIG. 1.

Depicted in FIGS. 1 and 2 is one embodiment of an expandable intervertebral implant 10 incorporating features of the present disclosure. Implant 10 is designed for placement and expansion between adjacent vertebra of a spine to facilitate fusion of the adjacent vertebra.

Figure 3:
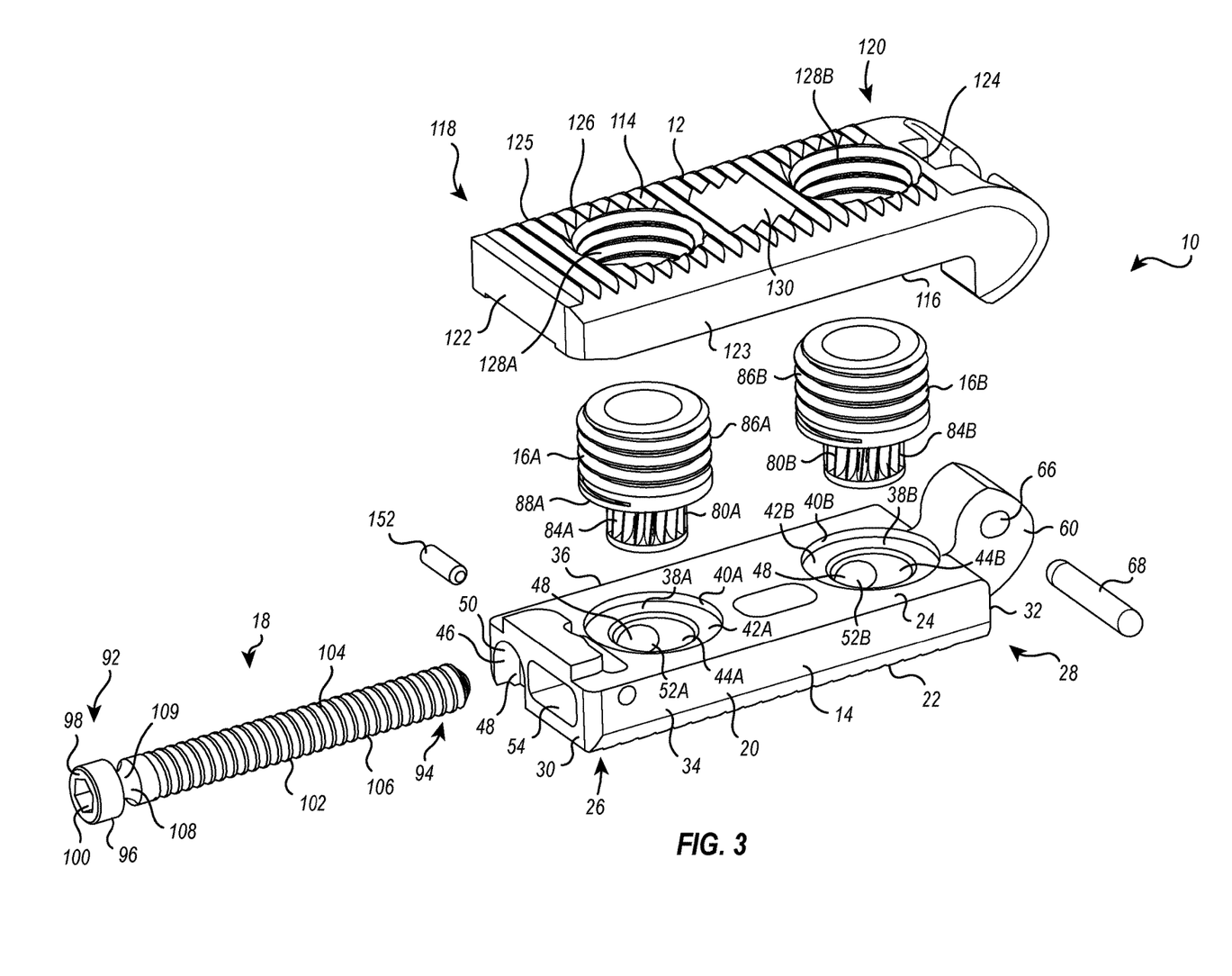
FIG. 3 is an exploded view of the implant shown in FIG. 1.

Turning to FIG. 3, implant 10 generally comprises a superior plate 12 that overlays an inferior plate 14. A first lift screw 16A and a second lift screw 16B are used to selectively raise and lower superior plate 12 relative to inferior plate 14. A drive screw 18 is used to selectively rotate lift screws 16A and 16B. Each of the above parts will now be discussed in great detail.

With continued reference to FIG. 3, inferior plate 14 comprises an inferior body plate 20 having a bottom surface 22 and an opposing interior surface 24 that longitudinally extend between a proximal end 26 and an opposing distal end 28. Proximal end 26 terminates at a proximal end face 30 while distal end 28 terminates at a distal end face 32. Body plate 20 also includes opposing side surfaces 34 and 36 that likewise extend between proximal end 26 and distal end 28.

As depicted in FIG. 2, a plurality of teeth 58 outwardly project from bottom surface 22 of inferior plate 14. Teeth 58 are used to facilitate securing inferior plate 14 to an adjacent vertebra. Bottom surface can be planar or can be curved, such as have a convex curvature.

Figure 4:
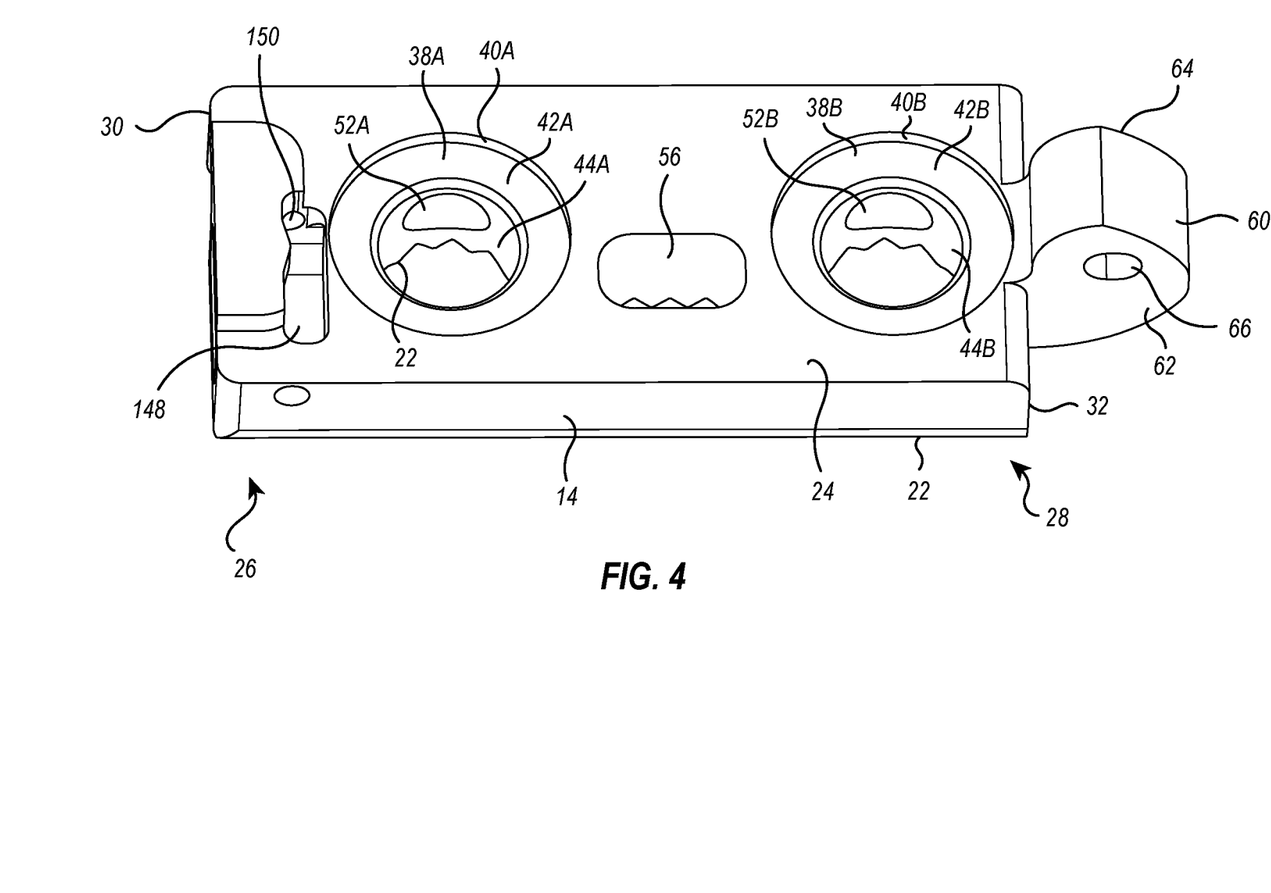
FIG. 4 is a top perspective view of the inferior plate of the implant shown in FIG. 3.

As depicted in FIG. 4, extending through body plate 20 between bottom surface 22 and interior surface 24 is a first bore 38A and a space apart second bore 38B. First bore 38A is disposed at or toward proximal end 26 and comprises a recess 40A that is recessed into interior surface 24 to annular shoulder 42A. Bore 38A also includes a passage 44A that centrally extends through shoulder 42A to bottom surface 22. In the embodiment depicted, recess 40A and passage 44A both have a cylindrical configuration and are concentrically aligned with passage 44A having a smaller diameter than recess 40A. Second bore 38B is disposed at or toward distal end 28 and is spaced apart from first bore 38A. Second bore 38B has the same configuration as first bore 38A and like elements are identified by like reference characters. However, the reference characters of second bore 38B incorporate the suffix "B".

With reference to FIG. 3, body plate 20 of inferior plate 14 also has an interior surface 46 that encircles and at least partially bounds a channel 48 that longitudinally extends between proximal end 26 and distal end 28 adjacent to side 36. In one embodiment, channel 48 has a cylindrical configuration. An opening 50 to channel 48 is formed on proximal end face 30. For reasons as will be discussed below in greater detail, bores 38A and 38B are formed so as to partially intersect with channel 48. As such, an opening 52A extends between first bore 38A/passage 44A and channel 48 while an opening 52B extends between second bore 38B/passage 44B and channel 48. An elongated slot 54 is also recessed into proximal end face 30 and is spaced apart from opening 50. Slot 54 is used to receive an inserter that can be used in the placement of implant 10. It is noted that bores 38A and 38B are typically not threaded but are designed to freely rotatably receive lift screws 16A and 16B.

As depicted in FIG. 4, a fill hole 56 is disposed between bores 38A and 38B and likewise extends between bottom surface 22 and interior surface 24. During use, fill hole 56 can be packed with an osteogenic material to facilitate the rapid growth of a bony column through implant 10 for fusing the adjacent vertebra. As used in the specification and appended claims, the term "osteogenic material" is broadly intended to include natural bone, such as autogenous bone graft or bone allograft, synthetic hone, growth factors and cytokines (including bone morphogenic proteins), and/or combinations thereof. FIG. 4 also shows a recesses 148 that is recessed into interior surface 24 of inferior plate 14 at a location between first bore 38A and proximal end face 30. Recess 148 reveals and provides access to a retention opening 150 that extends through inferior plate 14 from recess 148 to channel 48. As will be discussed below in greater detail, retention opening 150 is configured to receive a retention pin 152 (FIG. 3) that secures drive screw 18 within channel 48.

Figure 6:
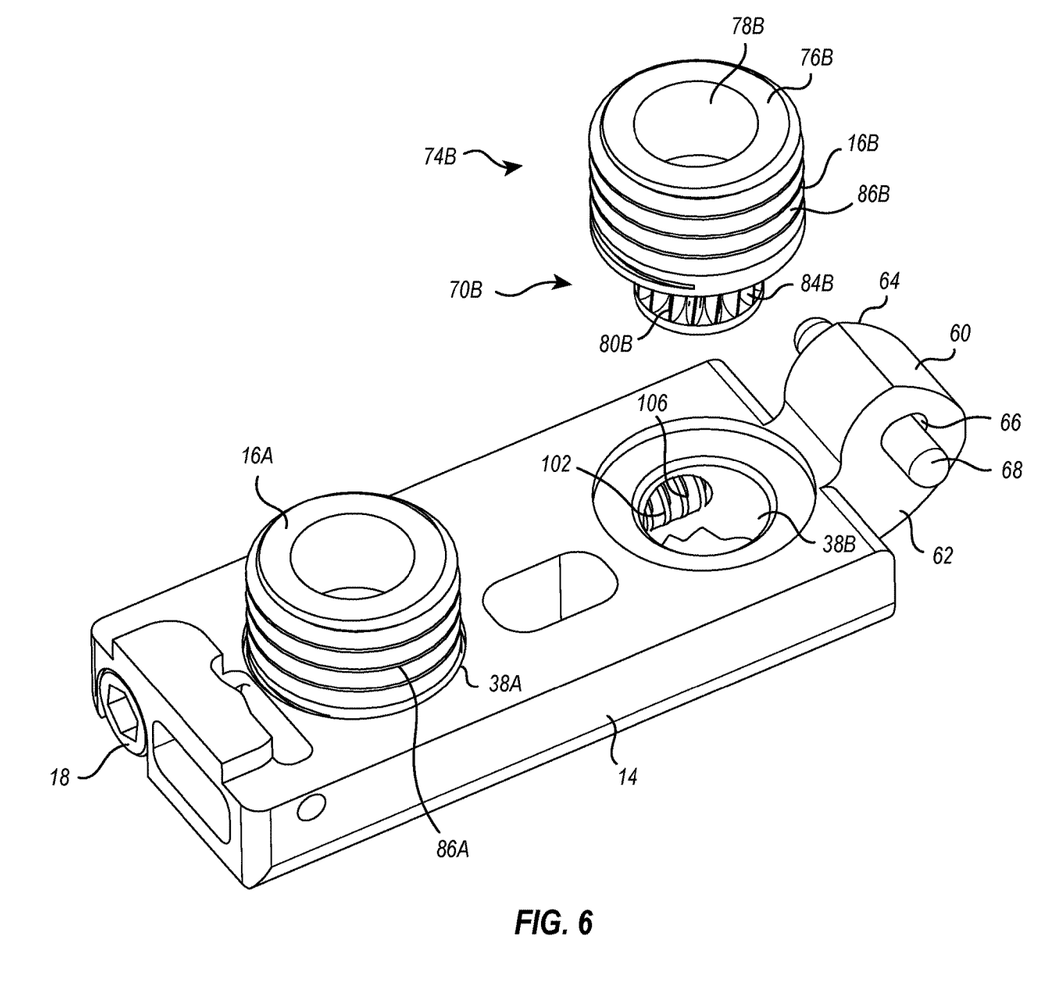
FIG. 6 is a perspective view of the implant shown in FIG. 3 in a partially assembled state.

Centrally outwardly projecting from distal end face 32 of inferior body plate 20 is a tongue 60 having opposing sides 62 and 64. A hole 66 passes through tongue 60 between opposing sides 62 and 64. Tongue 60 projects both distally from body plate 20 and upwardly towards superior plate 12. As shown in FIGS. 3 and 6, hole 66 is configured to receive a guide pin 68. Guide pin 68 is sized so that opposing ends of guide pin 68 can outwardly project from opposing sides 62 and 64 of tongue 60.

Figure 5:
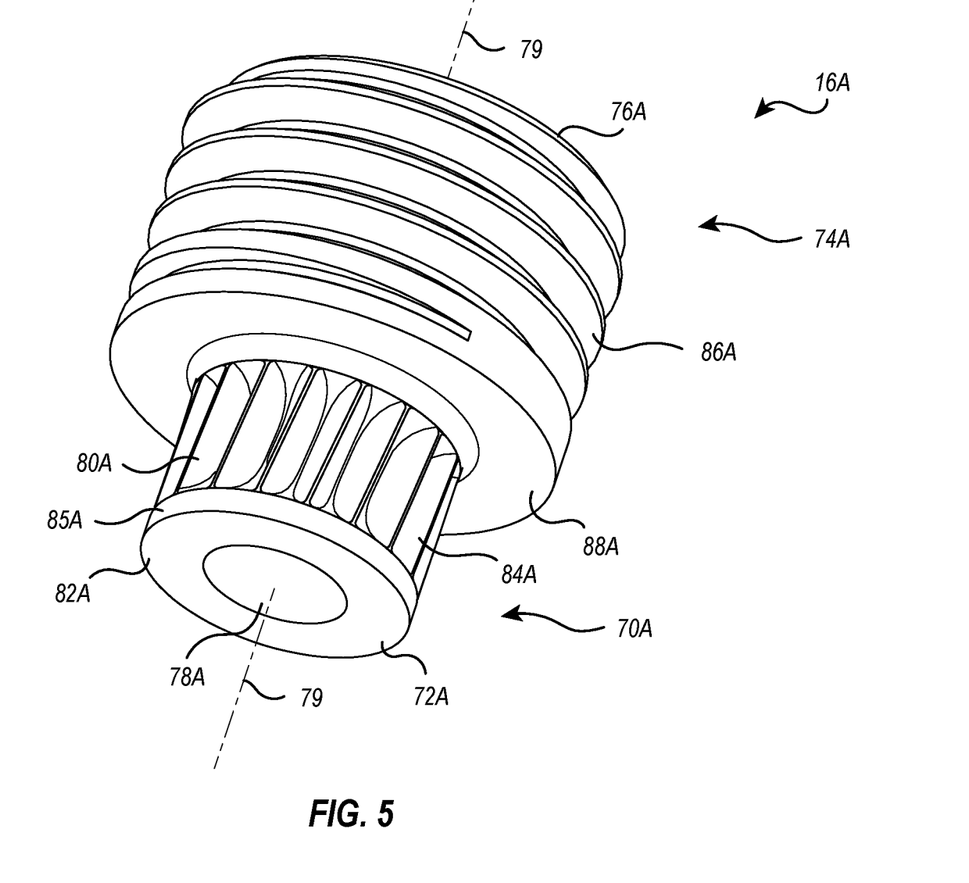
FIG. 5 is a perspective view of one of the lift screws of the implant shown in FIG. 3.

Turning to FIG. 5, first lift screw 16A generally has a first end 70A that terminates at a first end face 72A and an opposing second end 74A that terminates at a second end face 76A. A passage 78A extends entirely through first lift screw 16A between first end 70A and second end 74A and, more specifically, between first end face 72A and second end face 76A. Again, during use, passage 78A can be packed with an osteogenic material to facilitate the rapid growth of a bony column through implant 10 for fusing adjacent vertebra.

First lift screw 16A can further be defined as comprising a gear wheel 80A disposed at first end 70A. Gear wheel 80A has a cylindrical body 82A with a plurality of teeth 84A that are disposed around an outer perimeter of body 82A. Teeth 84A are typically linear and are orientated so as to longitudinally extend toward first end 70A and opposing second end 74A. Teeth 84A can be curved and can be sloped to a desired orientation. For example, teeth 84A can be sloped relative to a central longitudinal axis 79 of passage 78A. Teeth 84A are bounded at first end 70A by an annular stop plate 85A.

Projecting from gear wheel 80A is a threaded stem 86A. Gear wheel 80A and threaded stem 86A are concentric in that they commonly share central longitudinal axis 79. However, threaded stem 86A has a maximum outer diameter that is larger than a maximum outer diameter of gear wheel 80A. As a result, an annular shoulder 88A extends between gear wheel 80A and the perimeter surface of threaded stem 86A.

With reference to FIGS. 3 and 6, lift screw 16A is configured so that gear wheel 80A can be freely and rotatably received within passage 44A of first bore 38A and the lower end of threaded stem 86A can be freely and rotatably received within recess 40A of first bore 38A. In this configuration, shoulder 88A of lift screw 16A rests against shoulder 42A of inferior plate 14. With reference to FIG. 6, second lift screw 16B has the identical configuration to first lift screw 16A and thus like elements are identified by like reference characters. However, the references elements for second lift screw 16B include the suffix "B". Lift screw 16B is also configured to similarly fit within second bore 38B.

Returning to FIG. 3, drive screw 18 is elongated and longitudinally extends between a proximal end 92 and an opposing distal end 94. Disposed at proximal end 92 is a head 96 that terminates at a proximal end face 98. A blind socket 100 is recessed into proximal end face 98 and is configured to receive a driver for rotating drive screw 18. Typically, socket 100 has a polygonal configuration to assist in engaging the driver. However, other non-circular configurations can also be used. Drive screw 18 also includes an elongated worm 102 disposed at or toward distal end 94. Worm 102 includes an elongated shaft 104 having on or more helical gears 106 extending along the length thereof. An annular constricted neck 108 is formed between head 96 and worm 102 and is surrounded by an annular groove 109.

Drive screw 18 is configured so that it can be freely rotatably disposed within channel 48 of inferior plate 14. More specifically, bores 38A and 38B intersect with channel 48 so that when drive screw 18 is received within channel 48, worm 102 (more specifically, helical gears 106) projects into bores 38A and 38B through openings 52A and 52B, respectively. In turn, when lift screws 16A and 16B are received within bores 38A and 38B, respectively, worm 102 (more specifically, helical gears 106) engages with teeth 84 of gear wheels 80 so that rotation of drive screw 18 within channel 48 facilitates rotation of lift screws 16A and 16B within bores 38A and 38B, respectively.

Continuing with FIG. 3, superior plate 12 comprises a superior body plate 112 having a top surface 114 and an opposing interior surface 116 that longitudinally extend between a proximal end 118 and an opposing distal end 120. Proximal end 118 terminates at a proximal end face 122 while distal end 120 terminates at a distal end face 124. Superior body plate 112 also includes opposing side surfaces 123 and 125 that likewise extend between proximal end 118 and distal end 120.

Outwardly projecting from top surface 114 are a plurality of space apart teeth 126 that are used for engaging adjacent vertebra. A threaded first hole 128A extends through body plate 112 from top surface 114 to interior surface 116 at or towards proximal end 118. A threaded second hole 128B extends through body plate 112 between top surface 114 and interior surface 116 at our toward distal end 120. Threaded holes 128A and 128B are spaced apart from each other. Threaded hole 128A is configured to threadedly receive threaded stem 86A of lift screw 16A while threaded hole 128B is configured to threadedly received threaded stem 86B of lift screw 16B. A fill hole 130 extends through body plate 112 between top surface 114 and interior surface 116 and is disposed between threaded holes 128A and 128B. Again, fill hole 130 is configured to receive an osteogenic material for facilitating bone grow through implant 10 to facilitate fusing of adjacent vertebra.

Figure 7:
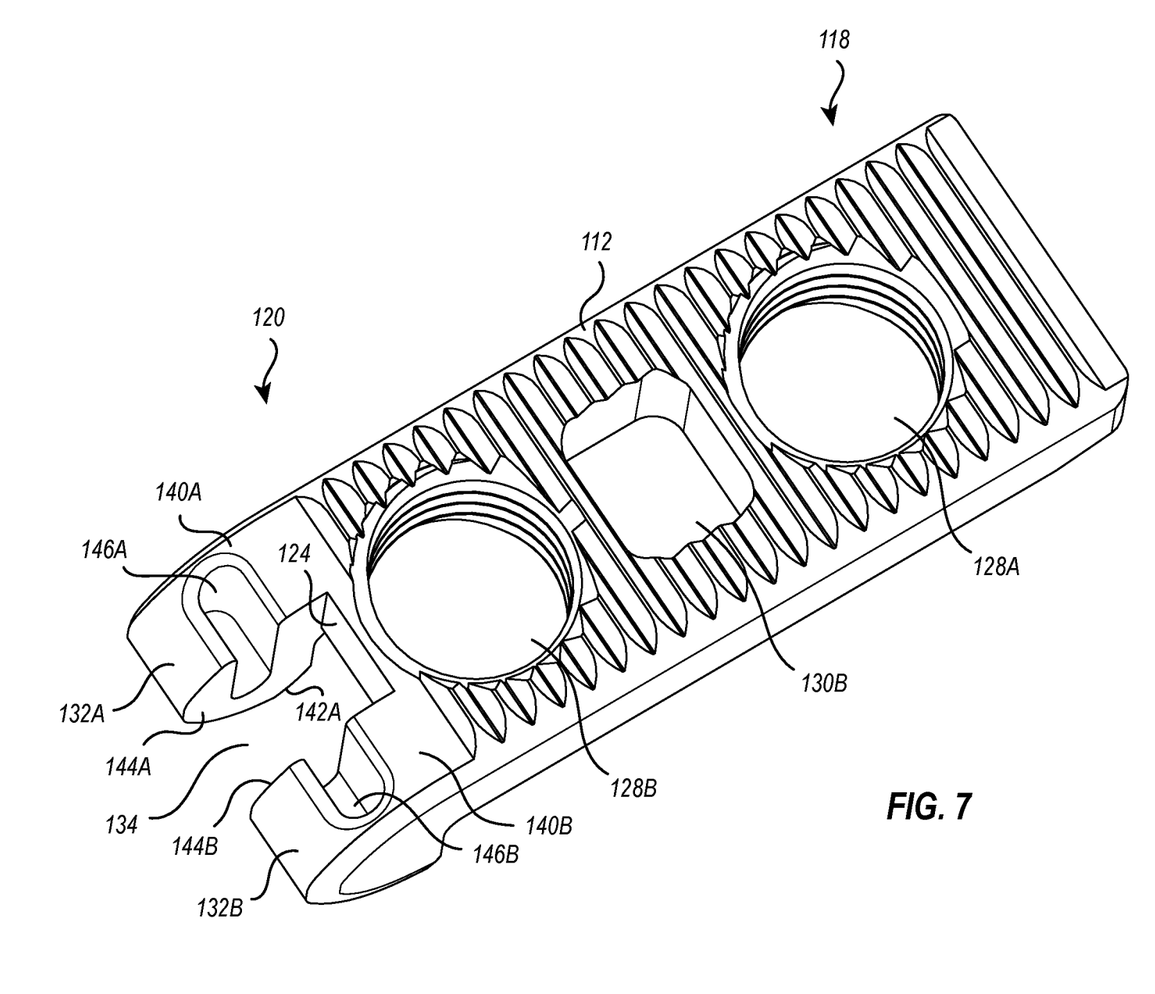
FIG. 7 is a top perspective view of the superior plate of the implant shown in FIG. 3.

Turing to FIG. 7, projecting from distal end face 124 of body plate 112 are a pair of spaced apart arms 132A and 132B. A gap 134 is formed between arms 132A and 132B and is configured to receive tongue 60 (FIG. 3) of inferior plate 14. Arms 132A and 132B project distally and downwardly towards inferior plate 14. Arm 132A has a top face 140A and an opposing bottom face 142A and an inside face 144A that extends therebetween. Inside face 144A faces arm 132B. A slot 146A is recessed into top face 140 and also passes through inside face 144A. Slot 146A is configured to freely slidably receive an end of guide pin 68 (FIG. 6). Arm 132B has the same configuration as arm 132A except that slots 146A and 146B are opposingly facing. Thus, like elements between arms 132A and 132B are identify like reference characters except that the reference characters for arm 132B include the suffix "B".

Implant 10 can be assembled in a variety of different ways. In one method of assembly, guide pin 68 is passed through hole 66 of tongue 60 of inferior plate 14 so that the opposing ends of guide pin 68 outwardly project from opposing sides of tongue 60, as shown in FIG. 6. Once guide pin 68 is positioned, superior plate 12 is inverted, relative to how shown in FIG. 3, and then advanced over inferior plate 14 so that tongue 60 is received within gap 134 between arms 132A and 132B and the opposing ends of guide pin 68 are received within slots 146A and 146B of arms 132A and 132B, respectively. Once guide pin 68 is received within slots 146A and 146B, superior plate 12 can be rotated to the orientation as shown in FIG. 1. Because of the depth of slots 146 and the configuration of tongue 60 and arms 132, it is appreciated that in the above described assembly shown in FIG. 1, superior plate 12 can be vertically raised and lowered relative to inferior plate 14 by guide pin 68 freely sliding within slots 146A and 146B. For example, superior plate 12 can be raised vertically relative to inferior plate 14 so that plates 12 and 14 remain in parallel or horizontal alignment. However, guide pin 68 prevents complete separation of superior plate 12 from inferior plate 14 by vertical raising of superior plate 12.

Either prior to or after coupling superior plate 12 to inferior plate 14 through the use of guide pin 68, lift screws 16A and 16B can be threaded into threaded holes 128A and 128B of superior plate 12 from interior surface 116. With lift screws 16 attached to superior plate 12, superior plate 12 can be advanced against inferior plate 14 (as shown in FIG. 1) so that gear wheels 80A and 80B (FIG. 3) are received within bores 38A and 38B, respectively. More specifically, gear wheels 80A and 80B are received within passages 44A and 44B, respectively, while lower ends of threaded stems 86A and 86B are received within recesses 40A and 40B, respectively. In this assembly shoulders 88 (FIG. 5) of lift screws 16 are sitting on shoulders 42 (FIG. 3) of inferior plate 14.

Once lift screws 16 are received within bores 38, drive screw 18 is advanced within channel 48 of inferior plate 14. As worm 102 reaches opening 52A that extends between first bore 38A and channel 48, helical gear 106 of worm 102 will strike against teeth 84A of gear wheel 80A. As such, to continue to advance drive screw 18, drive screw 18 is rotated. As drive screw 18 is rotated, helical gear 106 meshes with teeth 84A of gear wheel 80A which enables drive screw 18 to thread into channel 48. Drive screw 18 is further advanced by rotation into channel 48 so that worm 102 also meshes with teeth 84B of gear wheel 80B of lift screw 16B. Drive screw 18 is continued to advance until drive screw 18 is properly disposed within channel 48 and annular groove that encircles neck 108 is aligned with retention opening 150 (FIG. 4). Retention pin 152 is then press fit or otherwise secured within retention opening 150 to that retention pin 152 is at least partially disposed within annular grove 109 but does not interfere with the rotation of drive screw 18. As a result of retention pin 152 being received within annular groove 109, drive screw 18 can still be freely rotated within channel 48 but retention pin 152 blocks longitudinal movement of drive screw 18 within channel 48. That is, except for any play that retention pin 152 may have within annular groove 109, retention pin 152 prevents drive screw 18 from retracting out of or advancing further into channel 48.

Furthermore, worm 102 of drive screw 18 meshes with teeth 84 of gear wheels 80 at a location above corresponding stop plates 85 (FIG. 5). Stop plates 85 function to retain lift screws 16 within bores 38. That is, although lift screws 16 can freely rotate within bores 38, any lifting of lift screws 16 within bores 38 result in worm 102 striking against stop plates 85 which prevents any further lifting of lift screws 16. As such, stop plates 85 secure lift screws 16 within bores 38 by preventing lift screws 16 from being raised out of bores 38.

Figure 8:
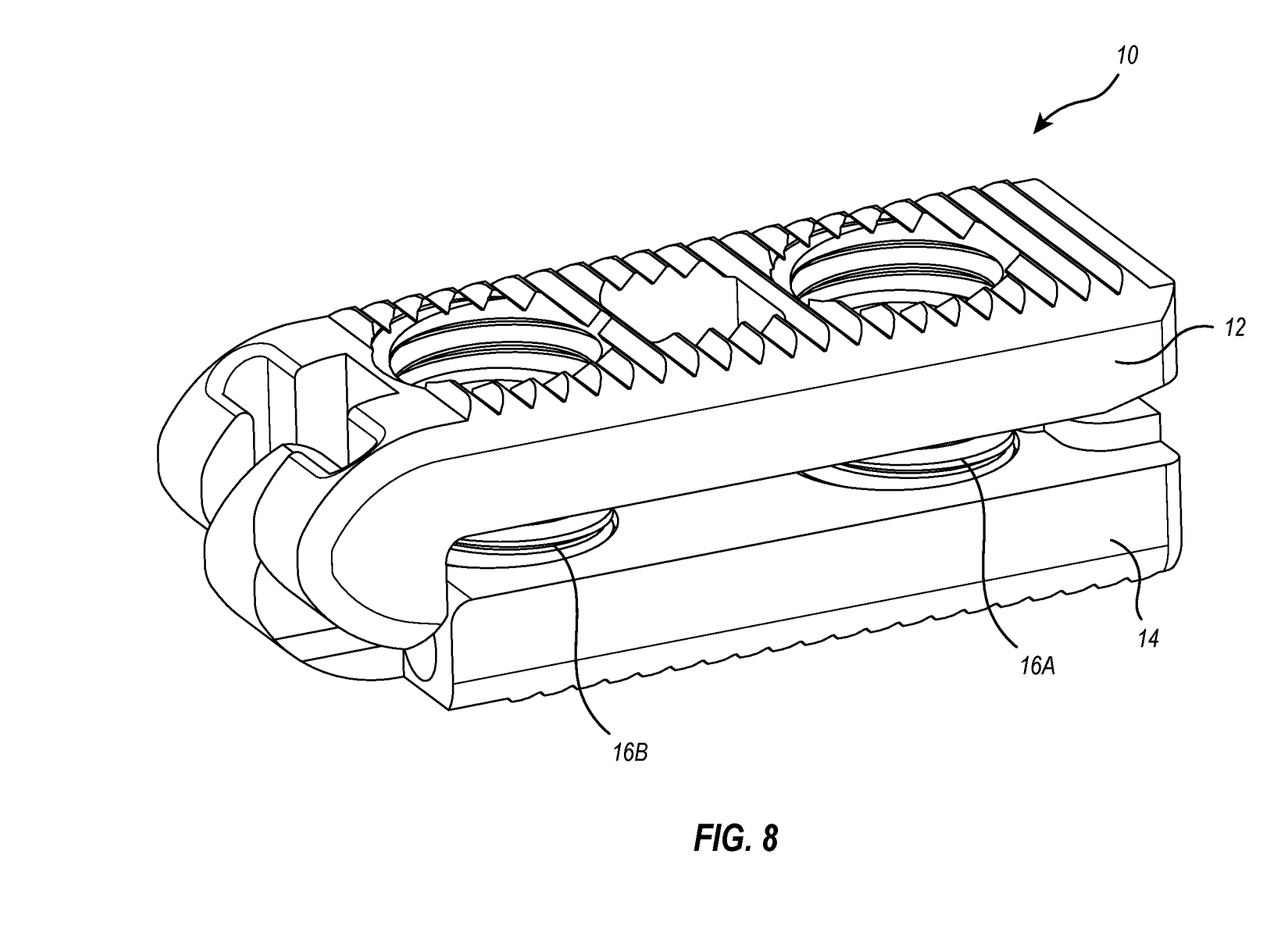
FIG. 8 is a top perspective view of the implant shown in FIG. 1 in an expanded state.

Implant 10 is now in a fully assembled configuration as shown in FIGS. 1 and 2. In this assembly, rotation of drive screw 18 in a first direction causes drive screw 18 to engage and concurrently rotate lift screw 16A and 16B in a first direction. In turn, the concurrent rotation of lift screw 16A and 16B causes superior plate 12, into which the lift screws 16A and B are threaded, to vertically rise relative to inferior plate 14, as shown in FIG. 8. In contrast, rotation of drive screw 18 in the opposite direction causes lift screws 16A and B to concurrently rotate in an opposite direction which in turn lowers superior plate 12 towards inferior plate 14, as shown in FIG. 1. Thus, by selectively rotating drive screw 18, implant 10 can be selectively moved between a collapsed position as shown in FIGS. 1 and 2 and an expanded position as shown in FIG. 8.

More specifically, as drive screw 18 is rotated in a first direction, helical gear 106 of worm 102 meshes with teeth 84 on gear wheel 80 to form a worm drive. Accordingly, because drive screw 18 is held stationary along its longitudinal direction, the rotation of drive screw 18 results in the concurrent rotation of gear wheels 80 in a first direction. In turn, the concurrent rotation of gear wheels 80 results in the simultaneous concurrent rotation of threaded stems 86 which, because lift screws 16/gear wheels 80 are held securely within bores 38, results in the raising or lowering of superior plate 12 relative to inferior plate 14. One of the advantages of use a worm drive is that by adjusting the size of worm 102 and gear wheels 80 and/or the gears/teeth thereon, the speed of movement and torque applied can be adjusted. As such, a mechanical advantage can be achieved through the use of the worm drive.

The extent to which superior plate 12 can be raised relative to inferior plate 14 is in part limited by the movement of guide pin 69 within slots 146 (FIG. 7). That is, once guide pin 69 hits against the bottom slots 146, further raising of superior plate 12 relative to inferior plate 14 is restrained.

Implant 10 can also be assembled in other ordered steps. For example, prior to or after attaching superior plate 12 to inferior plate 14 using guide pin 68, lift screws 16 can first be received within bores 38A and 38B and then secured in place by the insertion and locking of drive screw 18 within channel 48. Superior plate 12 can then be advanced on top of lift screw 16A and 16B which, when rotated by drive screw 18, thread into superior plate 12 so as to draw superior plate 12 towards inferior plate 14. Again, implant 10 can be selectively moved between the expanded and contracted position by selective rotating of drive screw 18. Other method steps of assembly can also be used.

Each of the components of implant 10 is made from a medical grade biocompatible material. In one embodiment, the components are molded from a reinforced polyetheretherketone (PEEK) polymer. For example, the components can be formed from a carbon fiber reinforced PEEK. In alternative embodiments, the components can be molded, cut, machined, or otherwise formed from medical grade biocompatible metals, polymers, ceramics, or other materials that have adequate strength. It is also appreciated that different components can be made from different materials. For example, the pins can be made of metal while the remainder is formed from a plastic.

During use, implant 10 is first moved to or towards that collapsed position. Osteogenic material can then be packed within passages 78A and 78B of lift screws 16 and within fill holes 56 and 130 of inferior plate 14 and superior plate 12, respectively. Here it is noted that fill holes 56 and 130 are aligned when implant 10 is assembly. As such, three separate bony columns can be formed that pass completely through implant 10 for fusing together the two adjacent vertebrae.

An insert tool is secured to implant 10 by being received within slot 54. The insert tool can also include a driver that engages with blind socket 100 of drive screw 18. The insert tool is then used to advance implant 10 between two adjacent vertebrae. Once implant 10 is properly positioned, the insert tool is used to rotate drive screw 18 which, as previously discussed, facilitates moving implant 10 from the contacted position to an expanded position. Implant 10 is selectively expanded until it is properly biased against the adjacent vertebra. Once implant 10 is sufficiently expanded, the insert tool is removed from the implant.

Embodiments of disclosed implant 10 can achieve a number of novel, unique, and/or beneficial properties. For example, because implant 10 is selectively expandable, it can be used in a variety of situations. As such, less storage of multiple different sizes of implants at a hospital is required. Furthermore, because the implant can be initially installed in a clasped position, which is smaller than is needed, implant 10 can be easily inserted. In addition, because the expansion of implant 10 only requires the rotation of drive screw 18, implant 10 can be easily expanded and requires a tool that occupies minimal space, thereby enable greater visual inspection of implant 10 during insertion and expansion.

Furthermore, by adjusting worm drive discussed herein, a mechanical advantage can be achieved in moving the implant from the collapsed position to the expanded position. Thus, less force can be required to be exerted by the surgeon while a greater force can be generated to expand and secure implant 10 between adjacent vertebra. The configuration of implant 10 is also unique in that it provides multiple separate channels extending completely through the implant through which osteogenic material can be packed for enabling bone to pass through implant 10 and fused together adjacent vertebra. Other benefits also exist.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, processes, products, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. An expandable intervertebral implant, the implant comprising:
   a superior plate having a top surface and an opposing interior surface that both extend between a proximal end and an opposing distal end, a threaded first hole extending through the superior plate between the top surface and the interior surface, a plurality of teeth outwardly projecting from the top surface;

an inferior plate having a proximal end, an opposing distal end, and a first bore, the inferior plate at least partially bounding an elongated channel that communicates with the first bore;

a first lift screw comprising a gear wheel rotatably received within the first bore of the inferior plate and a threaded stem projecting from the gear wheel and being threaded into the first hole of the superior plate;

a drive screw rotatably disposed within the channel of the inferior plate, the drive screw comprising a worm that engages with the gear wheel such that rotation of the drive screw facilitates rotation of the first lift screw which in turn facilitates movement of the superior plate relative to the inferior plate;

the superior plate or the inferior plate having a pair of spaced apart arms disposed at the distal end thereof with a gap being formed between the spaced apart arms; and the other of the superior plate or the inferior plate having a tongue disposed at the distal end thereof, the tongue being disposed within the gap between the pair of spaced apart arms so that when the drive screw is rotated in one direction, the entire superior plate moves away from the inferior plate.

2. The intervertebral implant of claim 1, further comprising:

the superior plate having a threaded second hole spaced apart from the first hole and extending through the superior plate between the top surface and the interior surface;

the inferior plate having a second bore spaced apart from the first bore;

a second lift screw comprising a gear wheel rotatably received within the second bore of the inferior plate and a threaded stem projecting from the gear wheel and being threaded into the second hole of the superior plate; and the worm of the drive screw engaging with the gear wheel of the second lift screw such that rotation of the drive screw facilitates simultaneous rotation of the first lift screw and the second lift screw.

3. The intervertebral implant of claim 2, further comprising:

a first fill hole extending through the superior plate between the top surface and the interior surface at a location between the threaded first hole and the threaded second hole.

4. The intervertebral implant of claim 3, wherein the first fill hole is not threaded.

5. The intervertebral implant of claim 2, wherein the inferior plate has a bottom surface and an opposing interior surface that both extend between the proximal end and the opposing distal end, the first bore extending through the inferior plate between the bottom surface and the interior surface, a plurality of teeth outwardly projecting from the bottom surface of the inferior plate.

6. The intervertebral implant of claim 5, further comprising:

the second bore extending through the inferior plate between the bottom surface and the interior surface; and a second fill hole extending through the inferior plate between the bottom surface and the interior surface at a location between the first bore and the second bore.

7. The intervertebral implant of claim 1, wherein the first bore is not threaded.

8. The intervertebral implant of claim 1, wherein the first lift screw has an interior surface that bounds a passage that passes entirely through the first lift screw so as to pass through the gear wheel and the threaded stem.

9. The intervertebral implant of claim 1, wherein the gear wheel of the first lift screw has a first maximum diameter and the threaded stem of the first lift screw has a second maximum diameter, the second maximum diameter being greater than the first maximum diameter.

10. The intervertebral implant of claim 1, wherein the channel longitudinally extends between the proximal end and the opposing distal end of the inferior plate.

11. The intervertebral implant of claim 1, wherein the first bore partially intersects with the channel.

12. The intervertebral implant of claim 1, wherein the proximal end of the inferior plate terminates at a proximal end face, an opening being formed on the proximal end face that communicate with the channel.

13. The intervertebral implant of claim 12, further comprising an elongated slot recessed into the proximal end face and spaced apart from the opening of the channel.

14. The intervertebral implant of claim 1, wherein the drive screw has a proximal end with a head formed thereat and an opposing distal end, a driver socket being recessed into the head.

15. The intervertebral implant of claim 1, further comprising:

each of the spaced apart arms having a top face and an opposing bottom face with an inside face extending therebetween, a slot being recessed into the top face and intersecting with the inside face; and a pin passing through the tongue, each opposing end of the pin being received within the slot of a corresponding one of the spaced apart arms.

16. The intervertebral implant of claim 1, further comprising a pin extending from the tongue and projecting into a slot formed on one of the spaced apart arms, the pin sliding along a length of the slot as the drive screw is rotated in the one direction.

17. The intervertebral implant of claim 16, wherein the length of the slot extends along an axis that is perpendicular to a longitudinal axis of the pin.

18. An expandable intervertebral implant, the implant comprising:

a superior plate having a proximal end, an opposing distal end, and a threaded first hole;

an inferior plate having a proximal end, an opposing distal end, and a first bore, the inferior plate at least partially bounding an elongated channel that communicates with the first bore;

a first lift screw comprising a gear wheel rotatably received within the first bore of the inferior plate and a threaded stem projecting from the gear wheel and being threaded into the first hole of the superior plate, the first lift screw having an interior surface that bounds a passage that passes entirely through the first lift screw so as to pass through the gear wheel and the threaded stem;

a drive screw rotatably disposed within the channel of the inferior plate, the drive screw comprising a worm that engages with the gear wheel such that rotation of the drive screw facilitates rotation of the first lift screw which in turn facilitates movement of the superior plate relative to the inferior plate;

the superior plate or the inferior plate having a pair of spaced apart arms disposed at the distal end thereof with a gap being formed between the spaced apart arms; and the other of the superior plate or the inferior plate having a tongue disposed at the distal end thereof, the tongue being disposed within the gap between the pair of spaced apart arms; and a guide pin outwardly projecting from the tongue and into a slot formed on one of the arms, the guide pin sliding along a length of the slot when the drive screw is rotated.

19. The intervertebral implant of claim 18, wherein the guide pin slides linearly along the length of the slot when the drive screw is rotated.

20. An expandable intervertebral implant, the implant comprising:

a superior plate having a proximal end, an opposing distal end, and a threaded first hole, a pair of spaced apart arms are disposed at the distal end with a gap slot formed between the spaced apart arms, each of the spaced apart arms having a top face and an opposing bottom face with an inside face extending therebetween, a slot being recessed into the top face and intersecting with the inside face;

an inferior plate having a proximal end, an opposing distal end, and a first bore, the inferior plate at least partially bounding an elongated channel that communicates with the first bore, the inferior plate further including a tongue disposed at the distal end and being received within the gap between the pair of spaced apart arms of the superior plate;

a first lift screw comprising a gear wheel rotatably received within the first bore of the inferior plate and a threaded stem projecting from the gear wheel and being threaded into the first hole of the superior plate;

a drive screw rotatably disposed within the channel of the inferior plate, the drive screw comprising a worm that engages with the gear wheel such that rotation of the drive screw facilitates rotation of the first lift screw which in turn facilitates movement of the superior plate relative to the inferior plate; and a pin passing through the tongue of the inferior plate so that opposing ends of the pin outwardly project from opposing ends of the tongue, each opposing end of the pin being received within the slot of a corresponding one of the spaced apart arms of the superior plate.

* * * * *